(12) United States Patent
Kobilka et al.

(10) Patent No.: US 10,214,693 B2
(45) Date of Patent: *Feb. 26, 2019

(54) FLAME-RETARDANT VANILLIN-DERIVED SMALL MOLECULES

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/584,866

(22) Filed: May 2, 2017

(65) Prior Publication Data

US 2018/0320076 A1 Nov. 8, 2018

(51) Int. Cl.
| | |
|---|---|
| *C09K 21/12* | (2006.01) |
| *C07C 15/04* | (2006.01) |
| *C07F 9/08* | (2006.01) |
| *C08K 5/5313* | (2006.01) |
| *C08K 5/5317* | (2006.01) |
| *C08K 5/5337* | (2006.01) |
| *C08K 5/372* | (2006.01) |

(52) U.S. Cl.
CPC .............. *C09K 21/12* (2013.01); *C07C 15/04* (2013.01); *C07F 9/08* (2013.01); *C08K 5/372* (2013.01); *C08K 5/5313* (2013.01); *C08K 5/5317* (2013.01); *C08K 5/5337* (2013.01)

(58) Field of Classification Search
CPC .......... C09K 21/12; C07C 15/04; C07F 9/08; C08K 5/5313; C08K 5/5337
USPC ......................................................... 524/27
See application file for complete search history.

(56) References Cited

FOREIGN PATENT DOCUMENTS

| CN | 107011499 A | 8/2017 |
|---|---|---|
| JP | 2013185039 A | 9/2013 |
| WO | 2016172353 A1 | 10/2016 |
| WO | 2017007883 A1 | 1/2017 |

OTHER PUBLICATIONS

Fache et al., Green Chemistry, 18, 712-725, 2016.*
Fache et al., "Epoxy thermosets from model mixtures of the lignin-to-vanillin process," Green Chemistry, 2016, 18, pp. 712-725, The Royal Society of Chemistry. DOI: 10.1039/c5gc01070e.
Fache et al., "Vanillin, a key-intermediate of biobased polymers," European Polymer Journal, 2015, vol. 68, pp. 488-502, Elsevier. DOI: 10.1016/j.eurpolymj.2015.03.050.
Fache et al., "Vanillin, a promising biobased building-block for monomer synthesis," Green Chemistry, 2014, 16, pp. 1987-1998, The Royal Society of Chemistry. DOI: 10.1039/c3gc42613k.
Illy et al., "Phosphorylation of bio-based compounds: the state of the art," Polymer Chemistry, 2015, 6 (35), pp. 6257-6291, The Royal Society of Chemistry DOI: 10.1039/c5py00812c.
Smolarski, N., "High-Value Opportunities for Lignin: Unlocking its Potential," Frost & Sullivan, Market Insight, Nov. 7, 2012, pp. 1-15.
Stanzione III, J., "S15.2. Vanillin: A Renewable and Versatile Platform Chemical for Sustainable Polymers," 14th International Symposium on Bioplastics, Biocomposites, and Biorefining, (May 31-Jun. 3, 2016), Jun. 22, 2016, pp. 1-26.
Kobilka et al., "Bondable Flame-Retardant Vanillin-Derived Molecules," U.S. Appl. No. 15/584,753, filed May 2, 2017.
Kobilka et al., "Flame-Retardant Vanillin-Derived Cross-Linkers," U.S. Appl. No. 15/584,798, filed May 2, 2017.
Kobilka et al., "Flame-Retardant Vanillin-Derived Monomers," U.S. Appl. No. 15/584,838, filed May 2, 2017.
List of IBM Patents or Patent Applications Treated as Related, Signed May 2, 2017, 2 pages.
Kobilka et al., "Bondable Flame-Retardant Vanillin-Derived Molecules," U.S. Appl. No. 15/850,681, filed Dec. 21, 2017.
Kobilka et al., "Flame-Retardant Vanillin-Derived Cross-Linkers," U.S. Appl. No. 15/850,738, filed Dec. 21, 2017.
Kobilka et al., "Flame-Retardant Vanillin-Derived Monomers," U.S. Appl. No. 15/850,784, filed Dec. 21, 2017.
Kobilka et al., "Flame-Retardant Vanillin-Derived Small Molecules," U.S. Appl. No. 15/850,838, filed Dec. 21, 2017.
List of IBM Patents or Patent Applications Treated as Related, Signed Dec. 21, 2017, 2 pages.

* cited by examiner

*Primary Examiner* — Hui H Chin
(74) *Attorney, Agent, or Firm* — Kelsey M. Skodje

(57) ABSTRACT

A flame-retardant vanillin-derived small molecule, a process for forming a flame-retardant polymer, and an article of manufacture comprising a material that contains the flame-retardant vanillin-derived small molecule are disclosed. The flame-retardant vanillin-derived small molecule can be synthesized from vanillin obtained from a bio-based source, and can have at least one phosphoryl or phosphonyl moiety with phenyl, allyl, or thioether substituents. The process for forming the flame-retardant polymer can include reacting a diol vanillin derivative and a flame-retardant phosphorus-based molecule to form the flame-retardant vanillin-derived small molecule, and binding the flame-retardant vanillin-derived small molecule to a polymer. The material in the article of manufacture can be flame-retardant, and contain the flame-retardant vanillin-derived small molecules. Examples of materials that can be in the article of manufacture can include resins, plastics, adhesives, polymers, etc.

7 Claims, 13 Drawing Sheets

F: DPCPa or DPCPo, 1. MgO, 2. cat. DMAP, DCM, reflux
G: 240-1 or 240-2, 1. MgO, 2. cat. DMAP, DCM, reflux

FLAME-RETARDANT VANILLIN-DERIVED SMALL MOLECULES

BACKGROUND

The present disclosure relates to bio-renewable flame-retardant compounds and, more specifically, flame-retardant vanillin-derived small molecules.

Bio-based compounds provide a source of renewable materials for various industrial applications, such as polymers, flame retardants, cross-linkers, etc. One example of a bio-based compound that can be used in these applications is vanillin (4-hydroxy-3-methoxybenzaldehyde). Vanillin is a plant metabolite and the main component of natural vanilla extract. While vanillin can be obtained from vanilla extract, or synthesized from petroleum-based raw materials, a number of biotechnology processes are also used to produce vanillin. These processes can be plant-based or microorganism-based, and provide a renewable source of vanillin on an industrial scale.

SUMMARY

Various embodiments are directed to flame-retardant vanillin-derived small molecules. The flame-retardant vanillin-derived small molecules can have at least one phosphoryl or phosphonyl moiety. Each phosphoryl or phosphonyl moiety can have at least one substituent selected from a group consisting of a phenyl substituent, an allyl substituent, and a thioether substituent. The flame-retardant vanillin-derived small molecules can be synthesized from vanillin obtained from a bio-based source. Additional embodiments are directed to forming a flame-retardant polymer. The polymer can be produced by forming a diol vanillin derivative, forming a phosphorus-based flame-retardant molecule, and reacting the diol vanillin derivative and the phosphorus-based flame-retardant molecule with one another to form a flame-retardant vanillin-derived small molecule. The flame-retardant vanillin-derived small molecule can then be combined with a polymer to form the flame-retardant polymer. The diol vanillin derivative can be a phenol diol vanillin derivative, a carboxylic acid diol vanillin derivative, or a benzyl alcohol diol vanillin derivative. The phosphorus-based flame-retardant molecule can be a phosphate-based molecule or a phosphonate-based molecule with at least one phenyl or allyl substituent. The phosphorus-based flame-retardant molecule can also be a thiol molecule, in some embodiments. The flame-retardant vanillin-derived small molecule can be combined with a polymer to form the flame-retardant polymer. Further embodiments are directed to an article of manufacture comprising a material that contains a flame-retardant vanillin-derived small molecule. The material can be a resin, plastic, adhesive, polymer, etc. Examples of polymer materials can include polyurethane, an epoxy, a polyhydroxyurethane, a polycarbonate, a polyester, a polyacrylate, a polyimide, a polyamide, a polyurea, and a poly(vinyl-ester).

DETAILED DESCRIPTION

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies include plant-based or microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant monomers or cross-linkers can be incorporated into polymers. Additionally, flame-retardant small molecules can be blended with the polymers.

Vanillin (4-hydroxy-3-methoxybenzaldehyde) is one example of a bio-based compound that can have applications as a component of various polymers, resins, and small molecules. Vanillin is a plant metabolite and the main component of natural vanilla extract. It can be obtained from the plant- and microorganism-based bio-sources discussed above, or synthesized from petroleum-based raw materials. According to some embodiments of the present disclosure, vanillin is used as a precursor for flame-retardant small molecules. The vanillin-based flame-retardant small molecules can be added to polymers, fabrics, resins, or other materials during blending, curing, foaming, extrusion, or other processing techniques. In addition to directly adding the vanillin-based flame-retardant small molecules to the materials during processing, the added vanillin-based flame-retardant small molecules can be contained within microcapsules.

Figure 1:
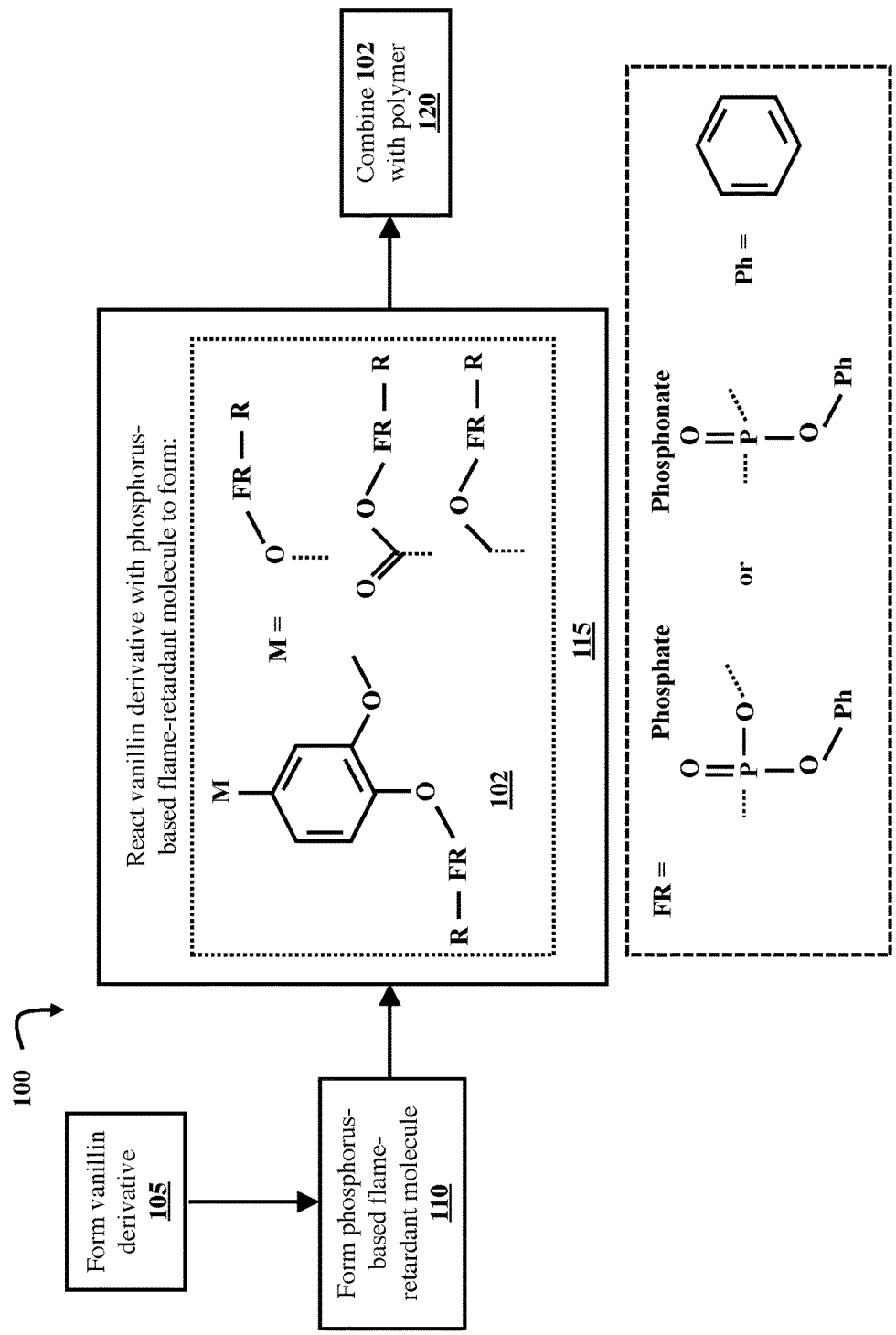
FIG. 1 is a flow diagram illustrating a process of forming a flame-retardant polymer containing a flame-retardant vanillin-derived small molecule, according to some embodiments of the present disclosure.

FIG. 1 is a flow diagram illustrating a process 100 of forming a flame-retardant polymer containing a vanillin-based flame-retardant small molecule 102, according to embodiments of the present disclosure. Process 100 begins with the formation of a diol vanillin derivative. This is illustrated at step 105. A diol is a molecule with two hydroxyl groups, and diol vanillin derivatives are formed when the aldehyde functional group on a vanillin molecule is replaced by a hydroxyl group or a substituent that contains a hydroxyl group. The identity of the substituent with the hydroxyl group is determined by the reaction conditions under which the diol derivative is produced. Examples of reaction conditions that can convert vanillin to a diol molecule can include oxidation by sodium percarbonate, oxidation by potassium permanganate, and reduction by sodium borohydride. The structures and syntheses of three examples of diol vanillin derivatives are discussed in greater detail with regard to FIG. 2A.

Process 100 continues with the formation of a phosphorus-based flame-retardant molecule. This is illustrated at step 110. The phosphorus-based flame-retardant molecule has either a phosphoryl or a phosphonyl moiety (collectively referred to as an FR group) with an attached R group. Examples of R groups that can be attached to an FR group include alkenes, phenyl groups, and thioethers. Examples of phosphorus-based flame-retardant molecules include phosphate- and phosphonate-based flame-retardant molecules, as well as flame-retardant thiol molecules that have FR groups. The structures and syntheses of phosphorus-based flame-retardant molecules are discussed in greater detail with regard to FIGS. 2B and 3A-3D. It should be noted that the formation of the phosphorus-based flame-retardant molecule of step 110 is illustrated as occurring after the formation of the diol vanillin derivative in step 105. However, in some embodiments, step 110 can occur before step 105.

The diol vanillin derivative and the phosphorus-based flame-retardant molecule are chemically reacted in order to form a vanillin-based flame-retardant small molecule 102. This is illustrated at step 115. The identity of the M group on the vanillin-based flame retardant small molecule 102 is determined by the diol vanillin derivative and the phosphorus-based flame-retardant molecule used in the reaction. The phosphorus-based flame-retardant molecules react with hydroxyl groups on the diol derivatives to provide the FR group with an attached R group. The identities of the FR and R groups on the generic vanillin-based flame-retardant small molecule 102 can vary. Examples of FR and R groups, as well as the syntheses and structures of vanillin-based flame-retardant small molecules 102, are discussed in greater detail with regard to FIGS. 4A-4F.

The vanillin-based flame-retardant small molecule 102 formed in step 115 is combined with a polymer, yielding a flame-retardant polymer. This is illustrated at step 120. In some embodiments, the vanillin-based flame-retardant small molecule 102 is combined with the polymer during the processing of the polymer. For example, flame-retardant vanillin-derived small molecules 102 can be added to a polymer during blending, curing, foaming, or extrusion processes.

The polymer to which the vanillin-based flame-retardant small molecule 102 is added can be petroleum-based, bio-based, a combination of petroleum- and bio-based, or any other synthetic or natural polymer. Examples of petroleum-based polymers that can be combined with the flame-retardant vanillin-derived small molecules 102 can include epoxies, polyurethanes, polyhydroxyurethanes, polycarbonates, polyesters, polyacrylates, polyimides, polyamides, polyureas, poly(vinyl-esters), etc. Examples of bio-based polymers that can be combined with flame-retardant vanillin-derived small molecules 102 can include starch-based plastics, cellulose-based plastics, protein-based plastics, etc. Further, the vanillin-based flame-retardant small molecule can be added to non-polymers in some embodiments.

Figure 2A:
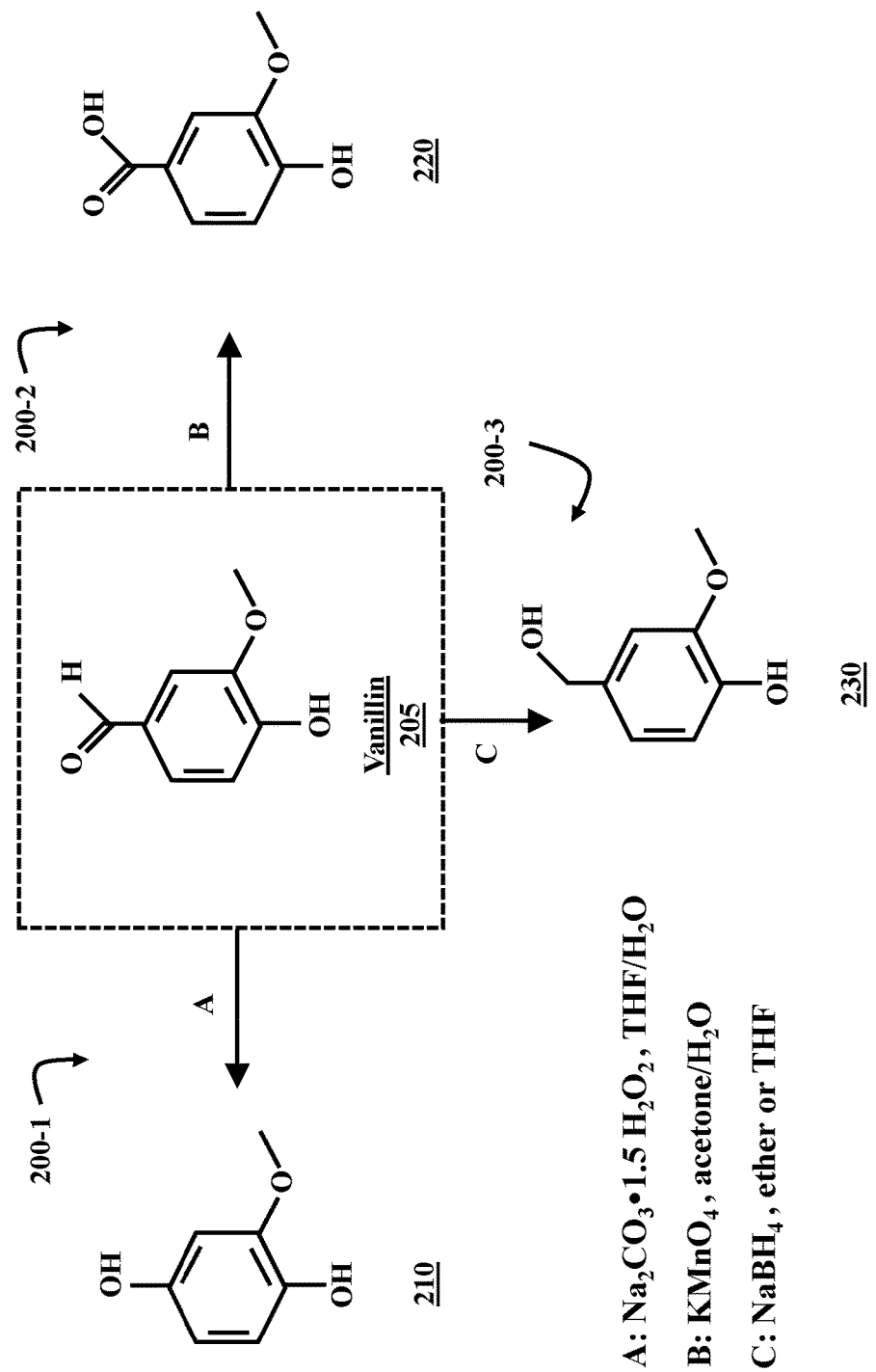
FIG. 2A is a chemical reaction diagram illustrating processes of synthesizing three diol vanillin derivatives, according to some embodiments of the present disclosure.

FIG. 2A is a chemical reaction diagram illustrating processes 200-1, 200-2, and 200-3 of synthesizing three diol compounds derived from vanillin, according to embodiments of the present disclosure. The three diol vanillin derivatives are a phenol diol derivative 210, a carboxylic acid diol derivative 220, and a benzyl alcohol diol derivative 230. The diol vanillin derivatives are precursors for the vanillin-based flame-retardant small molecules 102, as is described in greater detail with regard to FIGS. 4A, 4C, and 4E.

In process 200-1, the phenol diol derivative 210 of vanillin is produced in an oxidation reaction with sodium percarbonate. Deionized water is added to a solution of vanillin 205 in tetrahydrofuran (THF). The resulting vanillin/THF/$H_2O$ solution is degassed with an inert gas (e.g., argon or nitrogen). While agitating the mixture, sodium percarbonate ($Na_2CO_3 \cdot 1.5H_2O_2$) is added until pH=3 is reached, quenching the reaction. After quenching the reaction, the THF is evaporated, and the aqueous phase is extracted with ethyl acetate. The organic phases are collected, washed with brine, and dried over anhydrous sodium sulfate ($Na_2SO_4$). The ethyl acetate is removed under reduced pressure, yielding the isolated phenol diol derivative 210.

In process 200-2, the carboxylic acid diol derivative 220 of vanillin is produced in an oxidation reaction with potassium permanganate. Potassium permanganate ($KMnO_4$) is added to an acetone/H$_2$O solution of vanillin 205. The mixture is stirred for approximately 1.5 hours at room temperature. Sodium bisulfite (NaHSO$_3$) in hydrochloric acid (HCl) is added to the resulting purple mixture until the mixture is colorless. The mixture is extracted with ethyl acetate, and the organic phases are collected, washed with brine, and dried over anhydrous magnesium sulfate (MgSO$_4$). The ethyl acetate is removed under reduced pressure, yielding the isolated carboxylic acid diol derivative 220.

In process 200-3, the benzyl alcohol diol derivative 230 of vanillin is produced in a reduction reaction with sodium borohydride. Sodium borohydride (NaBH$_4$) is added to a solution of vanillin 205 in anhydrous ether or tetrahydrofuran (THF). The mixture is stirred at room temperature under an inert gas (e.g., argon or nitrogen) for approximately four hours. The mixture is then concentrated, and purified by column chromatography to give the benzyl alcohol diol derivative 230 as a colorless oil.

Figure 2B:
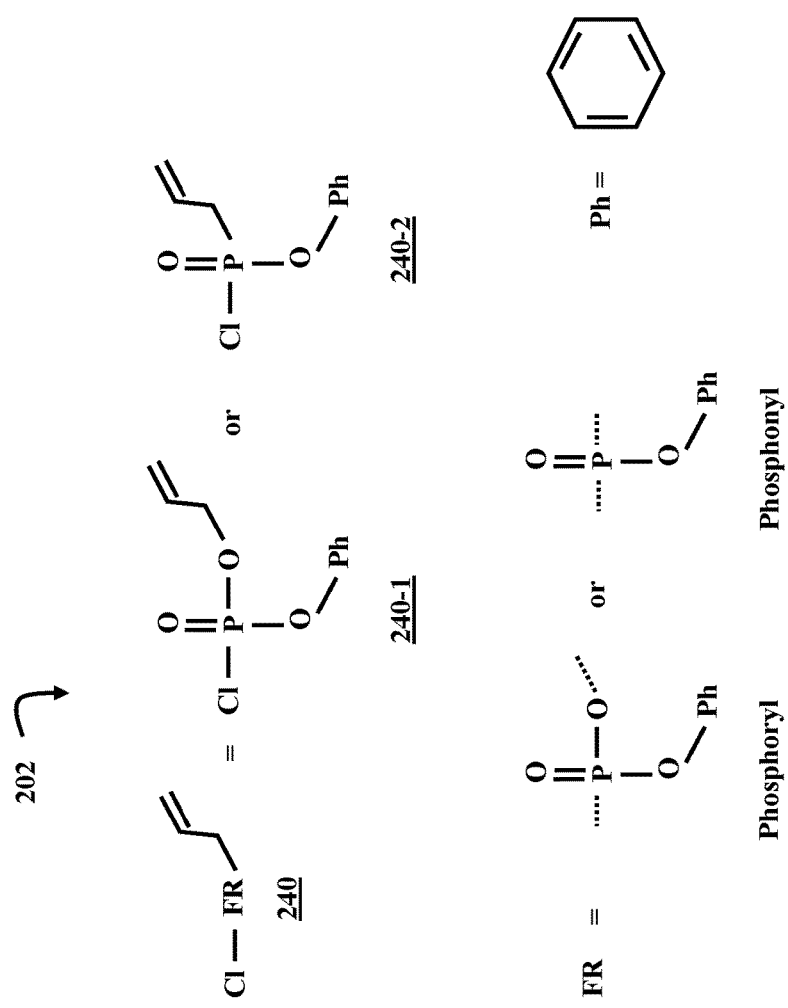
FIG. 2B is a diagrammatic representation of the molecular structures of generic phosphorus-based flame-retardant molecules, according to some embodiments of the present disclosure.

FIG. 2B is a diagrammatic representation of the molecular structures 202 of generic phosphorus-based flame-retardant molecules 240, according to embodiments of the present disclosure. Each phosphorus-based flame-retardant molecule 240 is either a phosphate-based flame-retardant molecule 240-1 or phosphonate-based flame-retardant molecule 240-2. Herein, phosphoryl and phosphonyl moieties are replaced by the abbreviation "FR" in order to simplify illustrations of the molecular structures. Each phosphorus-based flame-retardant molecule 240 has a phenyl (Ph) substituent and an allyl substituent. In some embodiments, the phenyl group is replaced by another alkyl substituent (e.g., methyl, ethyl, propyl, isopropyl, etc.). The syntheses of the phosphorus-based flame-retardant molecules 240 are discussed with regard to FIGS. 3A and 3B. The phosphorus-based flame-retardant molecules 240 are reacted with the vanillin diol derivatives 210, 220, and 230 to form vanillin-based flame-retardant small molecules 102. These reactions are discussed in greater detail with regard to FIGS. 4A, 4C, and 4E.

Figure 3A:
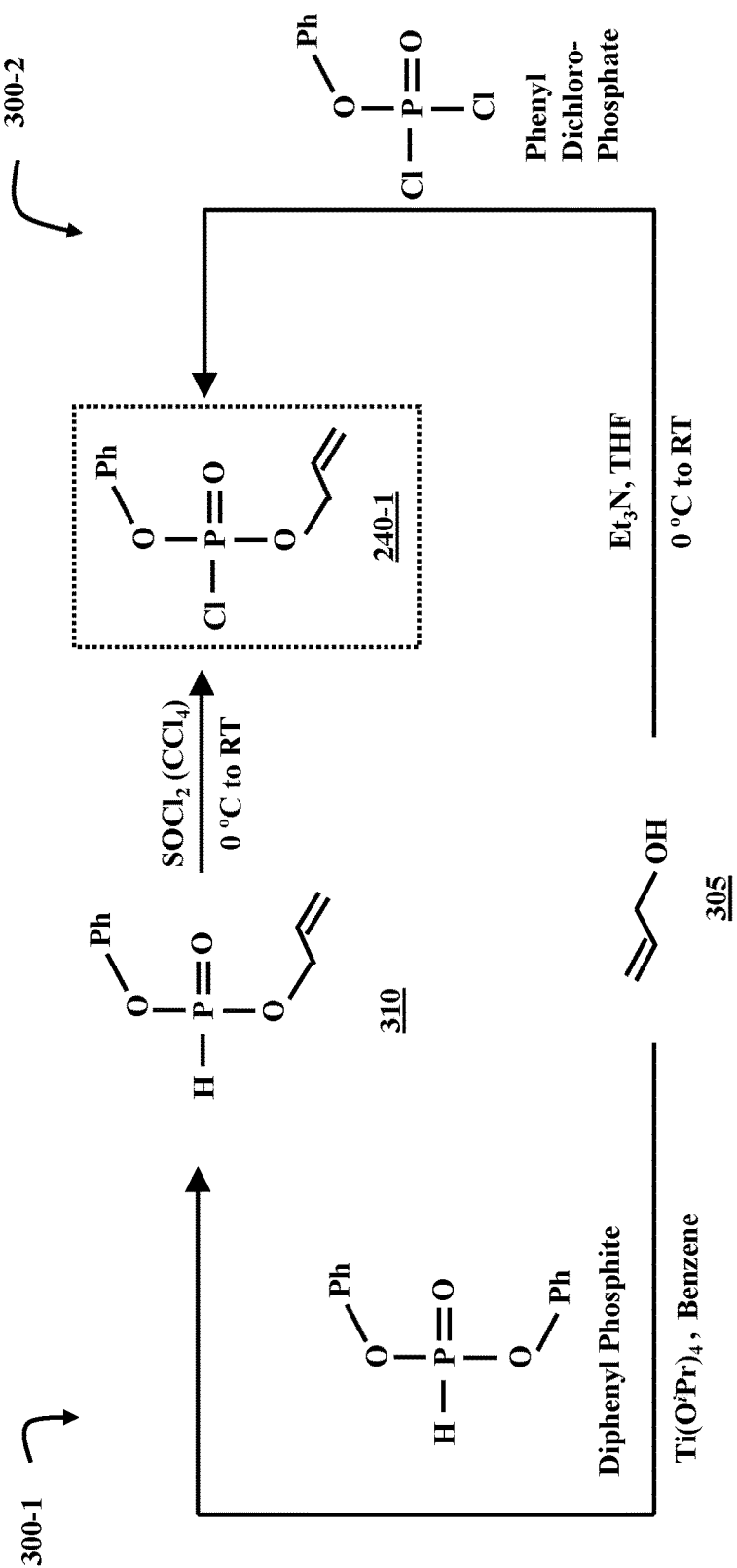
FIG. 3A is a chemical reaction diagram illustrating two processes of synthesizing the phosphate-based flame-retardant molecule, according to some embodiments of the present disclosure.

FIG. 3A is a chemical reaction diagram illustrating two processes 300-1 and 300-2 of synthesizing the phosphate-based flame-retardant molecule 240-1, according to embodiments of the present disclosure. In both processes 300-1 and 300-2, allyl alcohol 305 is a starting material for the phosphate-based flame-retardant molecule 240-1. It should be noted that, though allyl alcohol 305 is illustrated here, other alcohols with allylic chains of varying lengths (e.g., one to twelve methylene spacer groups) can be used. Additionally, alcohols with acrylate substituents are used in some embodiments.

In process 300-1, allyl alcohol 305 is reacted with diphenyl phosphite and titanium isopropoxide (Ti(O$^i$Pr)$_4$) in benzene to produce a precursor 310 to the phosphate-based flame-retardant molecule 240-1. In this pseudo-transesterification reaction, the precursor 310 is formed when a phenyl (Ph) substituent on diphenyl phosphite is replaced by the allyl group from the allyl alcohol 305. The precursor 310 is then reacted with thionyl chloride (SOCl$_2$) and carbon tetrachloride (CCl$_4$) over a range of 0° C. to room temperature (RT), forming the phosphate-based flame-retardant molecule 240-1.

In process 300-2, the allyl alcohol 305 is reacted with phenyl dichlorophosphate in a tetrahydrofuran (THF) solution containing triethyl amine (Et$_3$N). This reaction takes place over a range of 0° C. to room temperature (RT). A chloride on the phenyl dichlorophosphate is replaced by the allyl alcohol, resulting in the elimination of hydrogen chloride (HCl), which reacts with the triethyl amine. The addition of the allyl group to the phosphate molecule produces the phosphate-based flame retardant molecule 240-1.

Figure 3B:
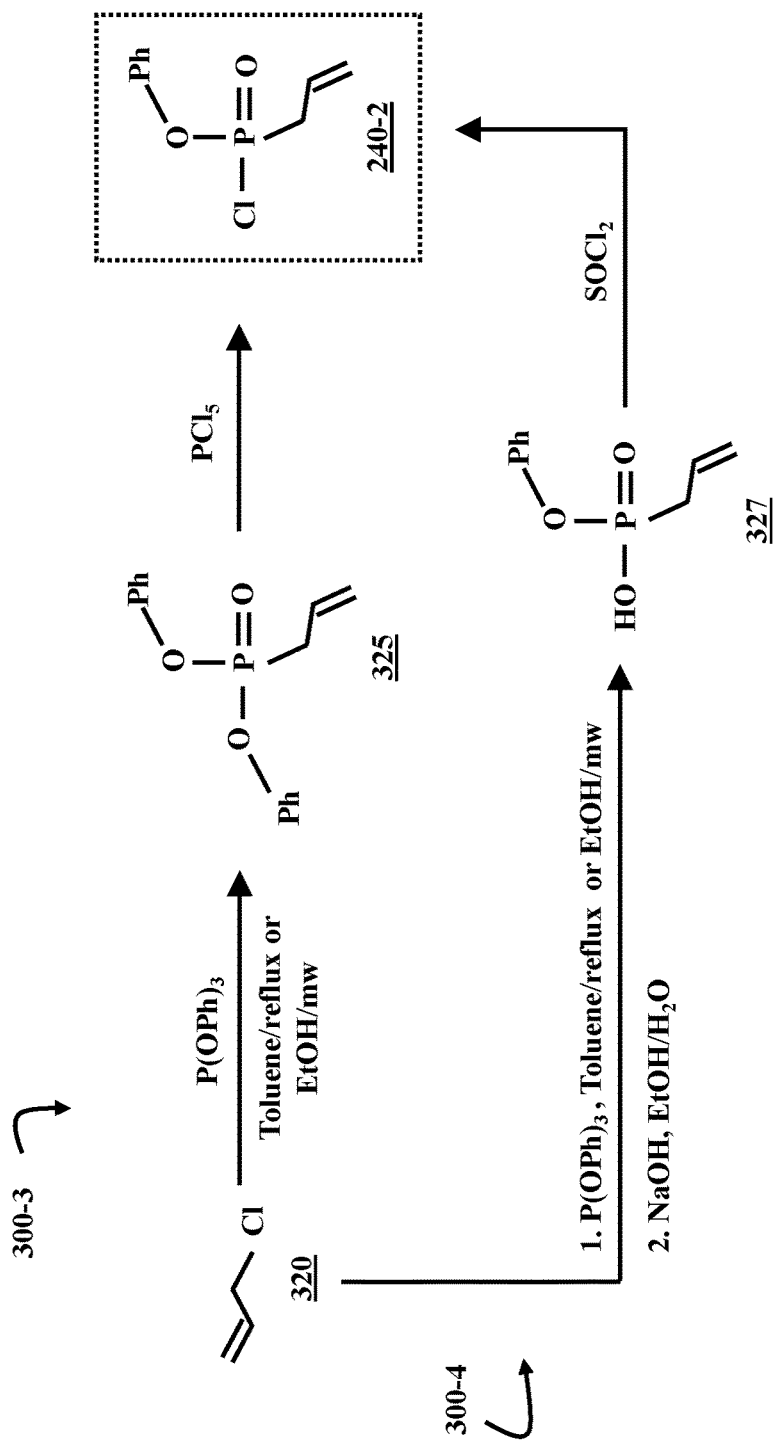
FIG. 3B is a chemical reaction diagram illustrating two processes of synthesizing the phosphonate-based flame-retardant molecule, according to some embodiments of the present disclosure.

FIG. 3B is a chemical reaction diagram illustrating two processes 300-3 and 300-4 of synthesizing the phosphonate-based flame-retardant molecule 240-2, according to embodiments of the present disclosure. In both processes 300-3 and 300-4, allyl chloride 320 is a starting material for the phosphonate-based flame-retardant molecule 240-2. It should be noted that, as discussed above in the case of the allyl alcohol 305, organochlorides or other organohalides with allylic chains of varying lengths (e.g., one to twelve methylene spacer groups) can be used. Additionally, organochlorides with acrylate substituents are used in some embodiments.

In process 300-3, the allyl chloride 320 is combined with triphenyl phosphite (P(OPh)$_3$). The mixture is heated, either by refluxing in toluene or microwaving (mw) in ethanol (EtOH), producing a phosphonyl ester precursor 325 to the phosphonate-based flame-retardant molecule 240-2. The phosphonyl ester precursor 325 is reacted with phosphorus pentachloride (PCl$_5$) to form the phosphonate-based flame-retardant molecule 240-2.

In process 300-4, a mixture of allyl chloride 320 and triphenyl phosphite (P(OPh)$_3$) is heated, either by refluxing in toluene or microwaving (mw) in ethanol (EtOH), producing a phenylphosphinic acid precursor 327 to the phosphonate-based flame-retardant molecule 240-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the phosphonate-based flame-retardant molecule 240-2.

Figure 3C:
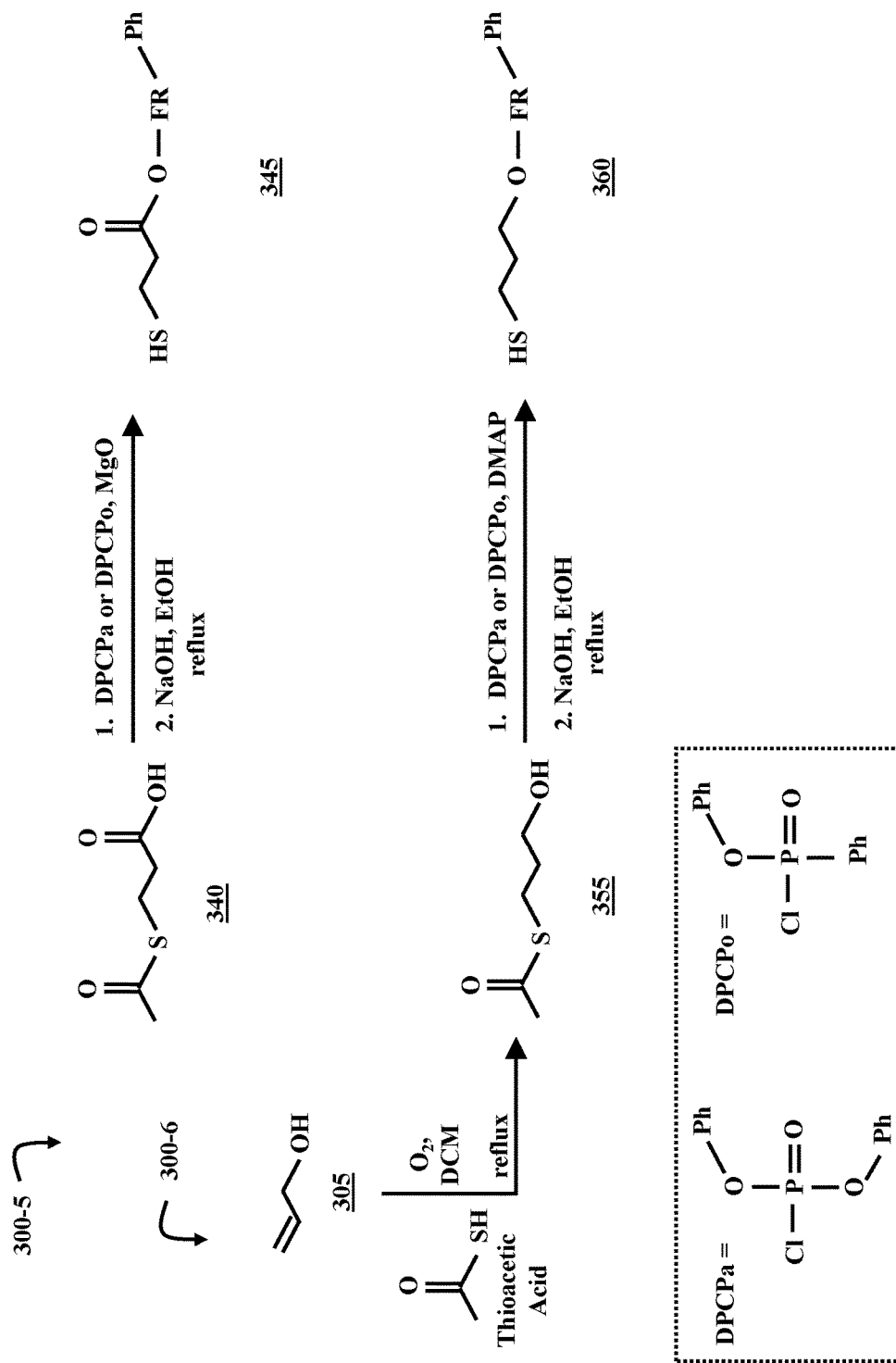
FIG. 3C is a chemical reaction diagram illustrating a process of synthesizing a carboxylic acid-derived flame-retardant thiol molecule and a process of synthesizing a hydroxy-derived flame-retardant thiol molecule, according to some embodiments of the present disclosure.

FIG. 3C is a chemical reaction diagram illustrating a process 300-5 of synthesizing a carboxylic acid-derived flame-retardant thiol molecule 345 and a process 300-6 of synthesizing a hydroxy-derived flame-retardant thiol molecule 360, according to embodiments of the present disclosure. In process 300-5, acetate-protected thiopropionic acid 340 is reacted with magnesium oxide (MgO) and diphenyl chlorophosphate (DPCPa) or diphenylphosphinic chloride (DPCPo). The acetate group is then removed by refluxing the mixture in an ethanol (EtOH) solution containing sodium hydroxide (NaOH), yielding the carboxylic acid-derived flame-retardant thiol molecule 345. If the process is carried out with DPCPa, the carboxylic acid-derived flame-retardant thiol molecule 345 will have phosphoryl FR groups, and, if the reaction is carried out with DPCPo, the carboxylic acid-derived flame-retardant thiol molecule 345 will have phosphonyl FR groups.

In process 300-6, allyl alcohol 305 is reacted with thioacetic acid in a thiol-ene reaction. In the first step of the reaction, oxygen (O$_2$) is added to a dichloromethane (DCM) solution of the allyl alcohol 305 and thioacetic acid. The mixture is refluxed, resulting in an acetate-protected mercaptopropanol 355. The second step in the reaction is a substitution reaction involving diphenyl chlorophosphate (DPCPa) and catalytic dimethylaminopyridine (DMAP) or diphenylphosphinic chloride (DPCPo). The acetate group is removed by refluxing the mixture in an ethanol (EtOH) solution containing sodium hydroxide (NaOH). This step results in the production of the hydroxy-derived flame-retardant thiol molecule 360. If the process is carried out with DPCPa, the hydroxy-derived flame-retardant thiol molecule 360 will have phosphoryl FR groups, and, if the reaction is carried out with DPCPo, the hydroxy-derived flame-retardant thiol molecule 360 will have phosphonyl FR groups.

Figure 3D:
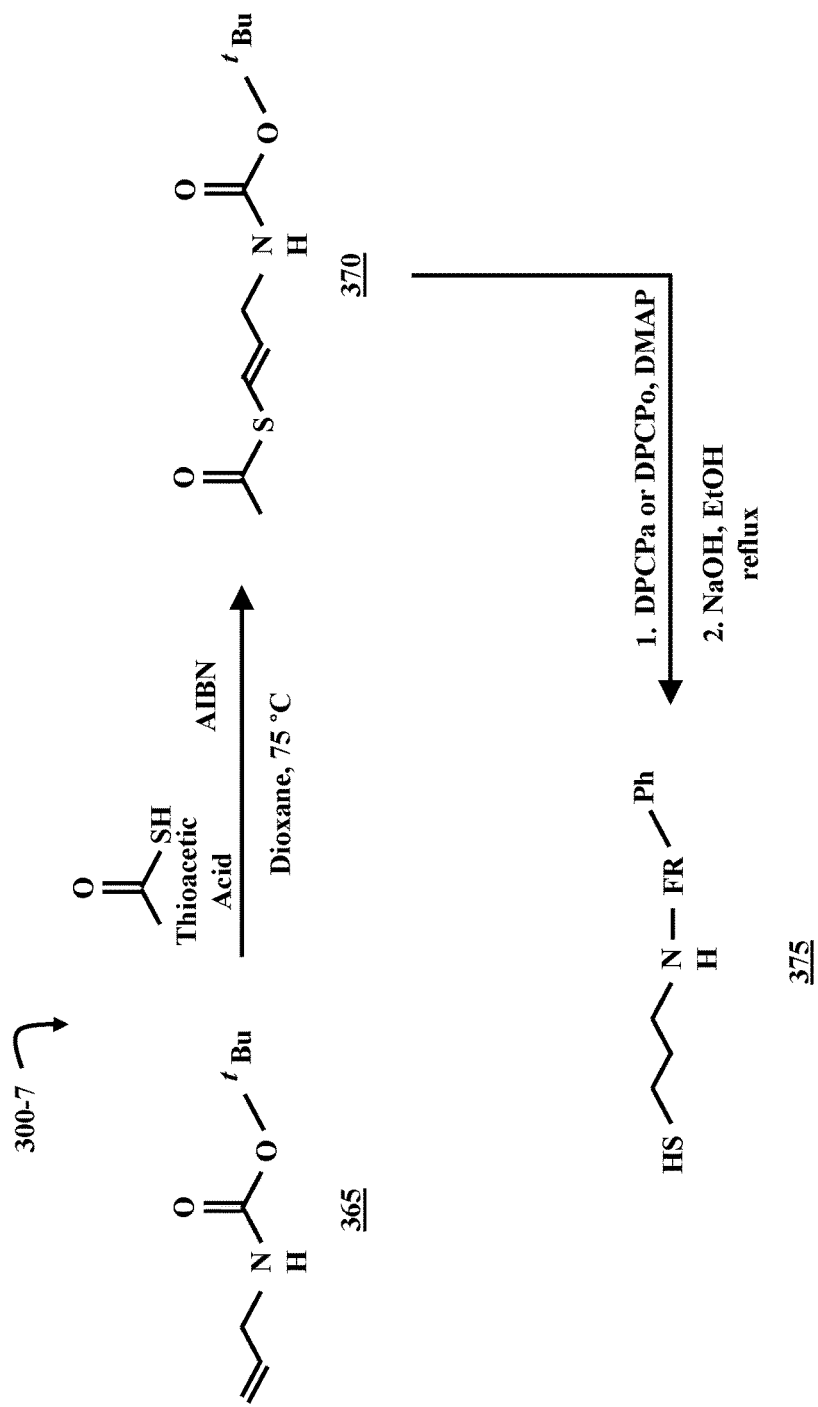
FIG. 3D is a chemical reaction diagram illustrating a process of synthesizing an amino-derived flame-retardant thiol molecule, according to embodiments of the present disclosure.

FIG. 3D is a chemical reaction diagram illustrating a process 300-7 of synthesizing an amino-derived flame-retardant thiol molecule 375, according to embodiments of the present disclosure. In process 300-7, 1-(boc-amino)-3-butene 365 is first reacted with thioacetic acid in a thiol-ene reaction. Azobisisobutyronitrile (AIBN) is added to the dioxane solution of 1-(boc-amino)-3-butene 365 and thioacetic acid, and the mixture is stirred at 75° C., resulting in an acetate-protected precursor 370 to the amino-derived flame-retardant thiol molecule 375. The second step in process 300-7 is a substitution reaction with diphenyl chlorophosphate (DPCPa) or diphenylphosphinic chloride (DPCPo) and catalytic dimethylaminopyridine (DMAP). The acetate group and boc groups are removed under basic conditions (e.g., by refluxing the mixture in an ethanol (EtOH) solution containing sodium hydroxide (NaOH)). This step results in the production of the amino-derived flame-retardant thiol molecule 375. If the process is carried out with DPCPa, the amino-derived flame-retardant thiol molecule 375 will have phosphoryl FR groups, and, if the reaction is carried out with DPCPo, the amino-derived flame-retardant thiol molecule 375 will have phosphonyl FR groups.

Figure 4A:
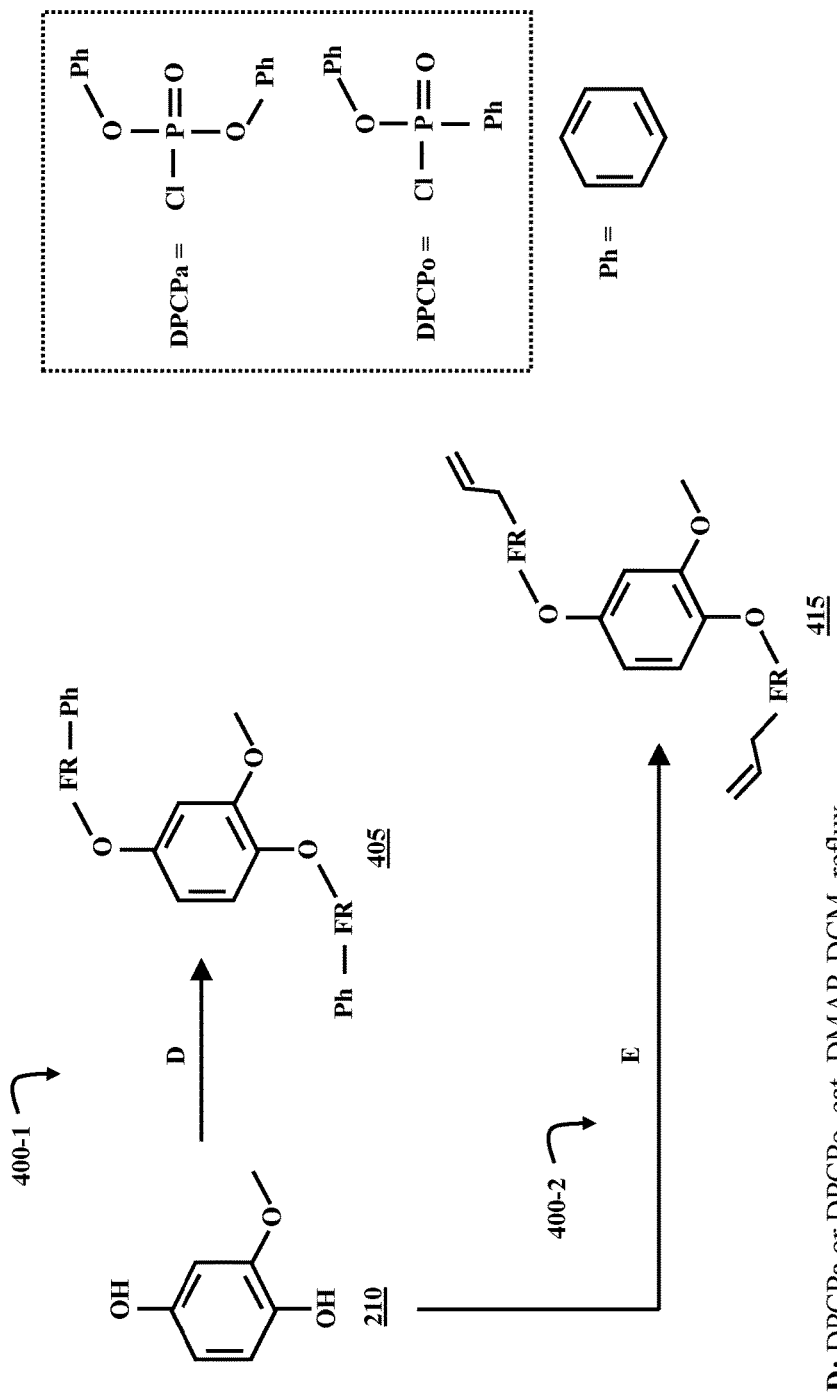
FIG. 4A is a chemical reaction diagram illustrating a process of synthesizing a phenyl-substituted flame-retardant phenol vanillin-derived small molecule and a process of forming an allyl-substituted flame-retardant phenol vanillin-derived small molecule, according to some embodiments of the present disclosure.

FIG. 4A is a chemical reaction diagram illustrating a process 400-1 of synthesizing a phenyl-substituted flame-retardant phenol vanillin-derived small molecule 405 and a process 400-2 of forming an allyl-substituted flame-retardant phenol vanillin-derived small molecule 415, according to embodiments of the present disclosure. In process 400-1, the phenol diol derivative 210 of vanillin is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, producing the phenyl-substituted flame-retardant phenol vanillin-derived small molecule 405. If the process is carried out with DPCPa, the phenyl-substituted phenol vanillin-derived small molecule 405 will have phosphoryl FR groups, and, if the reaction is carried out with DPCPo, the phenyl-substituted phenol vanillin-derived small molecule 405 will have phosphonyl FR groups.

In process 400-2, the phenol diol derivative 210 of vanillin is reacted with a phosphorus-based flame-retardant molecule 240 and catalytic dimethylaminopyridine (DMAP) in a dichloromethane (DCM) solution. The reaction between the phenol diol derivative 210 and the phosphate-based flame-retardant molecule 240 produces an allyl-substituted flame-retardant phenol vanillin-derived small molecule 415. If the reaction is carried out with phosphate-based flame-retardant molecule 240-1, the allyl-substituted flame-retardant phenol vanillin-derived small molecule 415 will have a phosphoryl FR group, and, if the reaction is carried out with the phosphonate-based flame-retardant molecule 240-2, the allyl-substituted flame-retardant phenol vanillin-derived small molecule 415 will have a phosphonyl FR group.

Figure 4B:
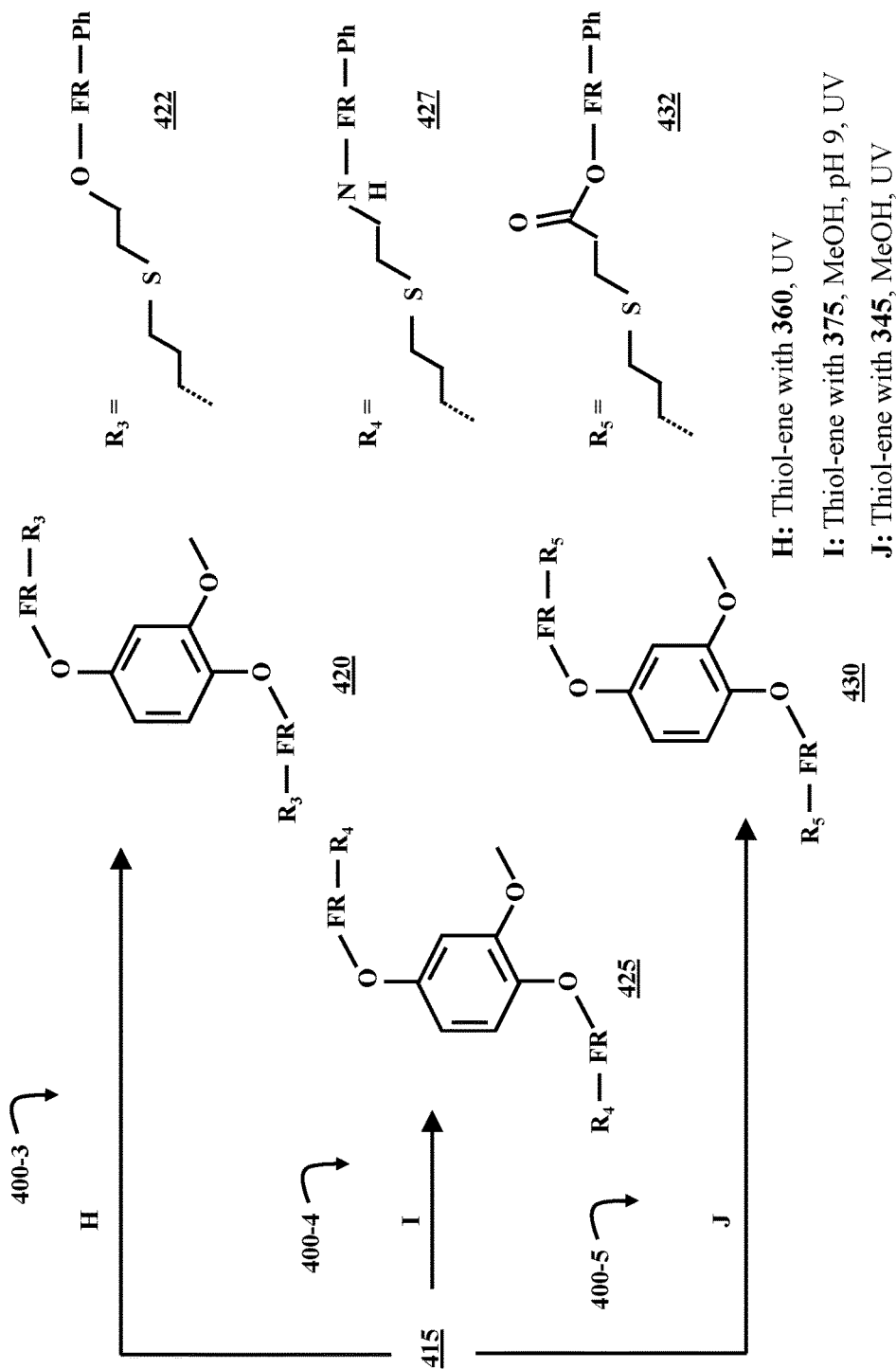
FIG. 4B is a chemical reaction diagram illustrating three processes of synthesizing thioether-linked flame-retardant phenol vanillin-derived small molecules, according to some embodiments of the present disclosure.

FIG. 4B is a chemical reaction diagram illustrating three processes 400-3, 400-4, and 400-5 of synthesizing thioether-linked flame-retardant phenol vanillin-derived small molecules, according to embodiments of the present disclosure. Each process is a thiol-ene reaction between the allyl-substituted flame-retardant phenol vanillin-derived small molecule 415 and a flame-retardant thiol molecule 345, 360, or 375. The syntheses and structures of the flame-retardant thiol molecules are discussed in greater detail with regard to FIGS. 3C and 3D.

In process 400-3, the allyl-substituted flame-retardant phenol vanillin-derived small molecule 415 is reacted with the hydroxy-derived flame-retardant thiol molecule 360 under UV light. The resulting thioether-linked flame-retardant phenol vanillin-derived small molecule 420 of vanillin has a thioether $R_3$ group 422 that corresponds to the hydroxy-derived flame-retardant thiol molecule 360. In process 400-4, the allyl-substituted flame-retardant phenol vanillin-derived small molecule 415 is reacted with the amino-derived flame-retardant thiol molecule 375 in a pH 9 methanol (MeOH) solution under UV light. The resulting thioether-linked flame-retardant phenol vanillin-derived small molecule 425 has a thio-ether $R_4$ group 427 that corresponds to the amino-derived flame-retardant thiol molecule 375. In process 400-5, the allyl-substituted flame-retardant phenol vanillin-derived small molecule 415 is reacted with the carboxylic acid-derived flame-retardant thiol molecule 345 under UV light in a methanol (MeOH) solution. The resulting thioether-linked flame-retardant phenol vanillin-derived small molecule 430 has a thio-ether $R_5$ group 432 that corresponds to the carboxylic acid-derived flame-retardant thiol molecule 345.

Figure 4C:
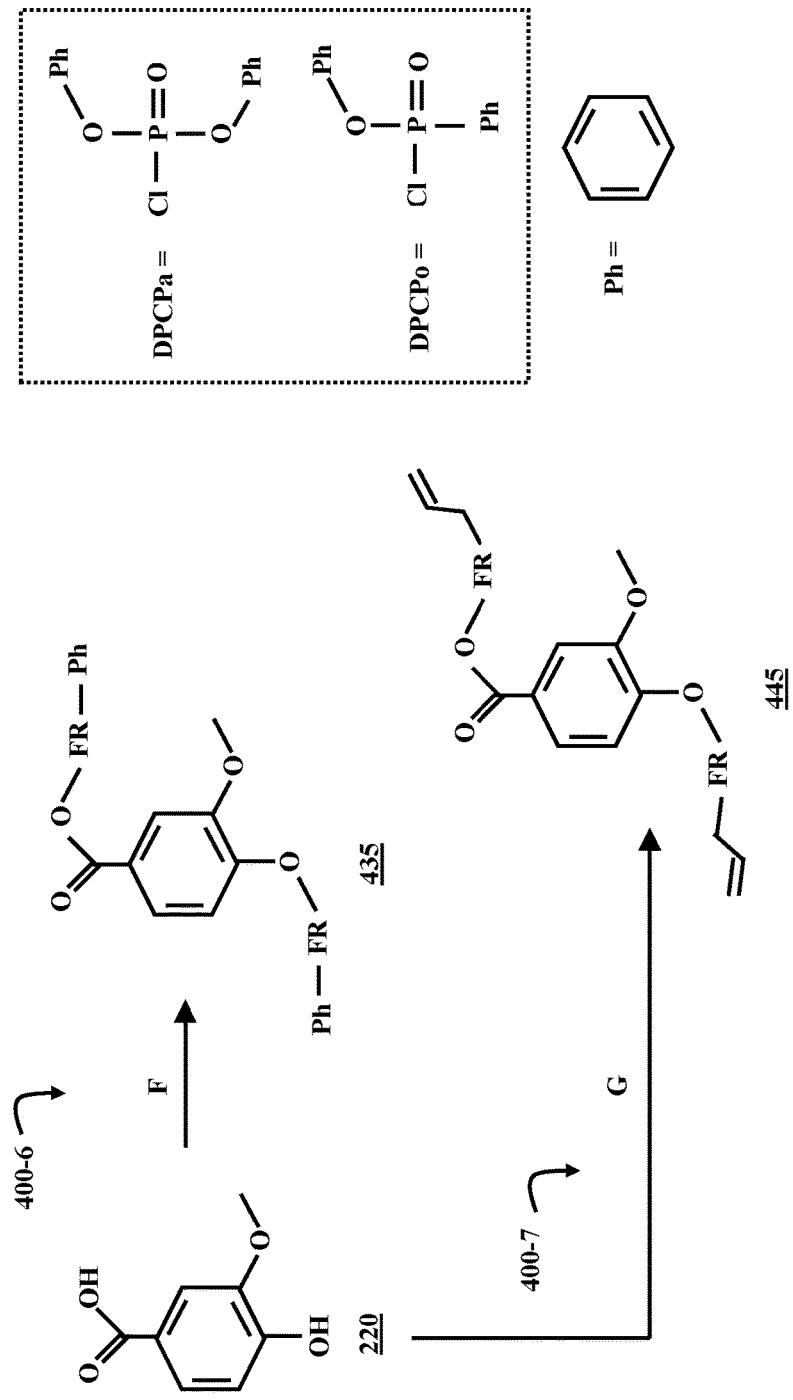
FIG. 4C is a chemical reaction diagram illustrating a process of synthesizing a phenyl-substituted flame-retardant carboxylic acid vanillin-derived small molecule and a process of forming an allyl-substituted flame-retardant carboxylic acid vanillin-derived small molecule, according to some embodiments of the present disclosure.

FIG. 4C is a chemical reaction diagram illustrating a process 400-6 of synthesizing a phenyl-substituted flame-retardant carboxylic acid vanillin-derived small molecule 435 and a process 400-7 of forming an allyl-substituted flame-retardant carboxylic acid vanillin-derived small molecule 445, according to embodiments of the present disclosure. In process 400-6, the carboxylic acid diol derivative 220 of vanillin is reacted with either diphenyl chlorophosphate (DPCPa) or diphenylphosphinic chloride (DPCPo). Magnesium oxide (MgO) is added to the reaction mixture. The mixture is then refluxed with catalytic dimethylaminopyridine (DMAP) in a dichloromethane (DCM) solution, producing the phenyl-substituted flame-retardant carboxylic acid vanillin-derived small molecule 435. If process 400-6 is carried out with DPCPa, the phenyl-substituted flame-retardant carboxylic acid vanillin-derived small molecule 435 will have a phosphoryl FR group, and, if the reaction is carried out with DPCPo, the phenyl-substituted flame-retardant carboxylic acid vanillin-derived small molecule 435 will have a phosphonyl FR group.

In process 400-7, the carboxylic acid diol derivative 220 of vanillin is combined with a phosphorus-based flame-retardant molecule 240 in a dichloromethane (DCM) solution. Magnesium oxide (MgO) is then added to the solution, and the mixture is refluxed with catalytic DMAP. The reaction between the carboxylic acid diol derivative 220 and the phosphorus-based flame-retardant molecule 240 produces the allyl-substituted flame-retardant carboxylic acid vanillin-derived small molecule 445 of vanillin. If the reaction is carried out with the phosphate-based flame-retardant molecule 240-1, the allyl-substituted flame-retardant carboxylic acid vanillin-derived small molecule 445 will have a phosphoryl FR group, and, if the reaction is carried out with the phosphonate-based flame-retardant molecule 240-2, the allyl-substituted flame-retardant carboxylic acid vanillin-derived small molecule 445 will have a phosphonyl FR group.

Figure 4D:
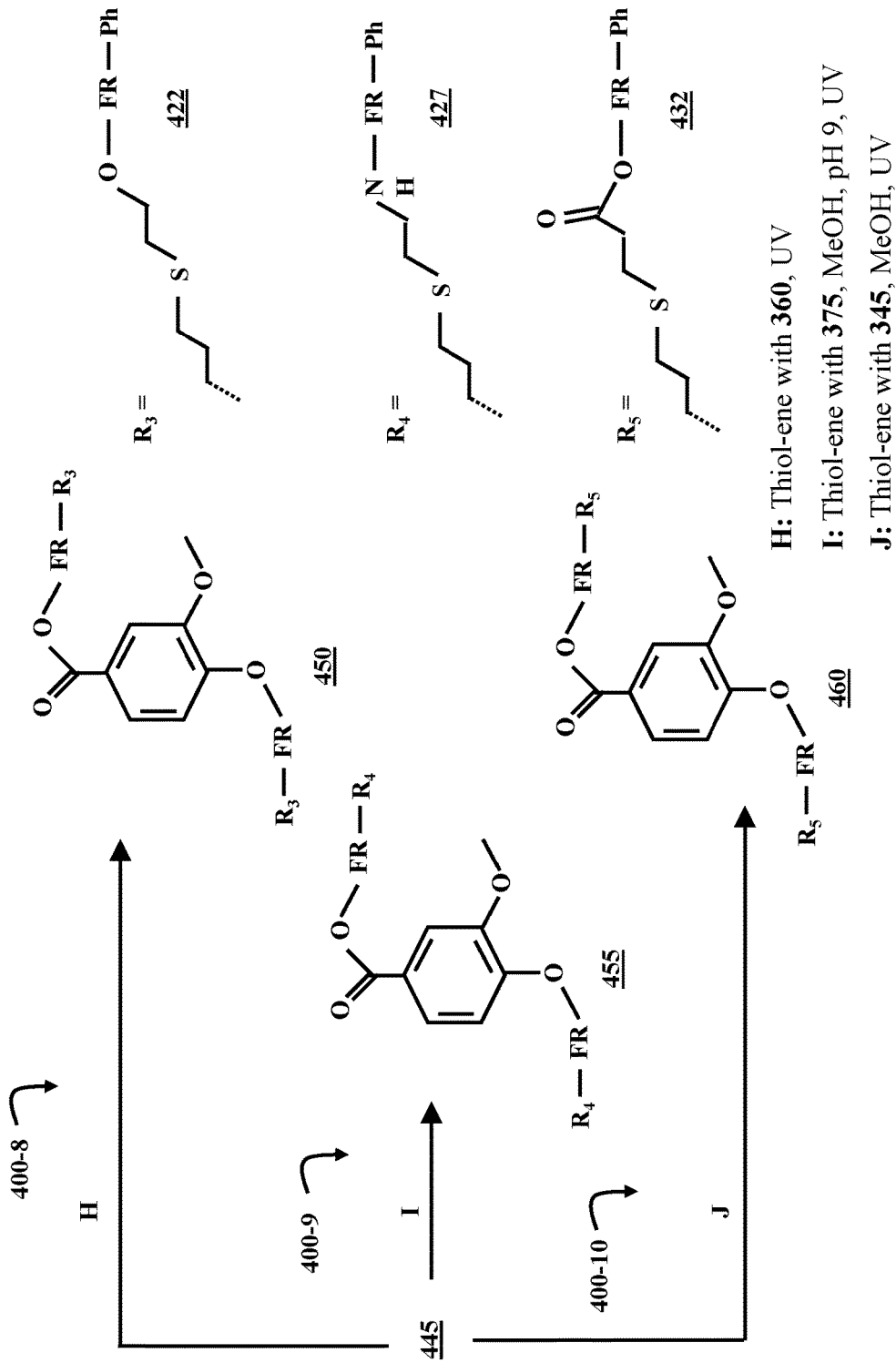
FIG. 4D is a chemical reaction diagram illustrating three processes of synthesizing thioether-linked flame-retardant carboxylic acid vanillin-derived small molecules, according to some embodiments of the present disclosure.

FIG. 4D is a chemical reaction diagram illustrating three processes 400-8, 400-9, and 400-10 of synthesizing thioether-linked flame-retardant carboxylic acid vanillin-derived small molecules, according to embodiments of the present disclosure. Each process is a thiol-ene reaction between the allyl-substituted flame-retardant carboxylic acid vanillin-derived small molecule 445 and a flame-retardant thiol molecule 345, 360, 375. The syntheses and structures of the flame-retardant thiol molecules are discussed in greater detail with regard to FIGS. 3C and 3D.

In process 400-8, the allyl-substituted flame-retardant carboxylic acid vanillin-derived small molecule 445 is reacted with the hydroxy-derived flame-retardant thiol molecule 360 under UV light. The resulting thioether-linked flame-retardant carboxylic acid vanillin-derived small molecule 450 has an $R_3$ group 422 that corresponds to the hydroxy-derived flame-retardant thiol molecule 360. In process 400-9, the allyl-substituted flame-retardant carboxylic acid vanillin-derived small molecule 445 is reacted with the amino-derived flame-retardant thiol molecule 375 in a pH 9 methanol (MeOH) solution under UV light. The resulting thioether-linked flame-retardant carboxylic acid vanillin-derived small molecule 455 has an $R_4$ group 427 corresponding to the amino-derived flame-retardant thiol molecule 375. In process 400-10, the allyl-substituted flame-retardant carboxylic acid vanillin-derived small molecule 445 is reacted with the carboxylic acid-derived flame-retardant thiol molecule 345 under UV light in a methanol (MeOH) solution. The resulting thioether-linked flame-retardant carboxylic acid vanillin-derived small molecule 460 has an $R_5$ group 432 corresponding to the carboxylic acid-derived flame-retardant thiol molecule 345.

Figure 4E:
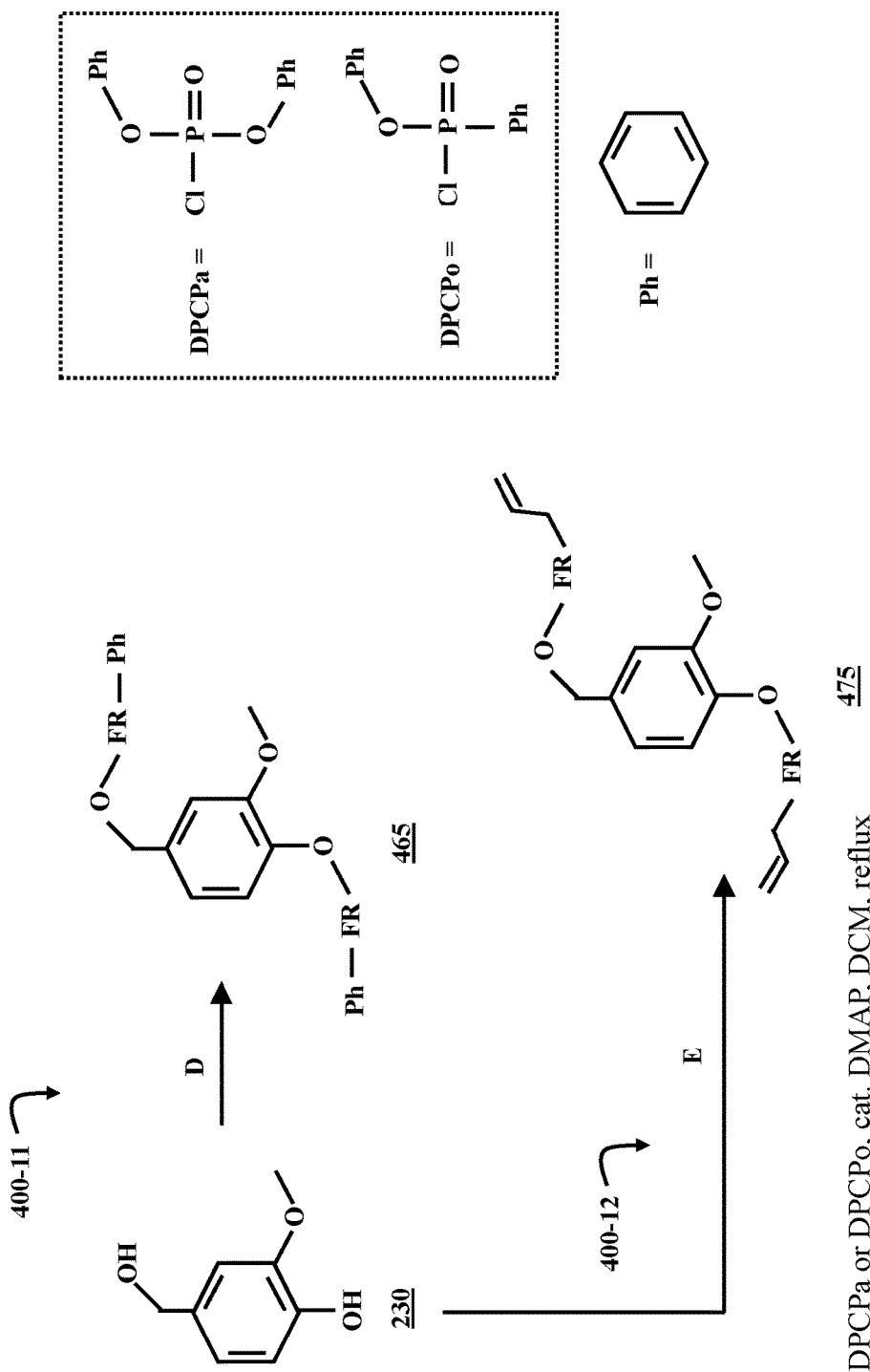
FIG. 4E is a chemical reaction diagram illustrating a process of synthesizing a phenyl-substituted flame-retardant benzyl alcohol vanillin-derived small molecule and a process of forming an allyl-substituted flame-retardant benzyl alcohol vanillin-derived small molecule, according to some embodiments of the present disclosure.

FIG. 4E is a chemical reaction diagram illustrating a process 400-11 of synthesizing a phenyl-substituted flame-retardant benzyl alcohol vanillin-derived small molecule 465 and a process 400-12 of forming an allyl-substituted flame-retardant benzyl alcohol vanillin-derived small molecule 475, according to embodiments of the present disclosure. In process 400-11, the benzyl alcohol diol derivative 230 of vanillin is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, producing the phenyl-substituted flame-retardant benzyl alcohol vanillin-derived small molecule 465. If the reaction is carried out with DPCPa, the phenyl-substituted flame-retardant benzyl alcohol vanillin-derived small molecule 465 will have a phosphoryl FR group, and, if the reaction is carried out with DPCPo, the phenyl-substituted flame-retardant benzyl alcohol vanillin-derived small molecule 465 will have a phosphonyl FR group.

Process 400-12 produces an allyl-substituted flame-retardant benzyl alcohol vanillin-derived small molecule 465. The benzyl alcohol diol derivative 230 of vanillin is reacted with a phosphorus-based flame-retardant molecule 240 and catalytic DMAP in a dichloromethane (DCM) solution. The reaction between the benzyl alcohol diol derivative 230 and the phosphorus-based flame-retardant molecule 240 produces the allyl-substituted flame-retardant benzyl alcohol vanillin-derived small molecule 465. As in the case of the flame-retardant phenol vanillin-derived small molecule 405, if the reaction is carried out with the phosphate-based flame-retardant molecule 240-1, the allyl-substituted flame-retardant benzyl alcohol vanillin-derived small molecule 475 will have a phosphoryl FR group, and, if the reaction is carried out with the phosphonate-based flame-retardant molecule 240-2, the allyl-substituted flame-retardant benzyl alcohol vanillin-derived small molecule 475 will have a phosphonyl FR groups.

Figure 4F:
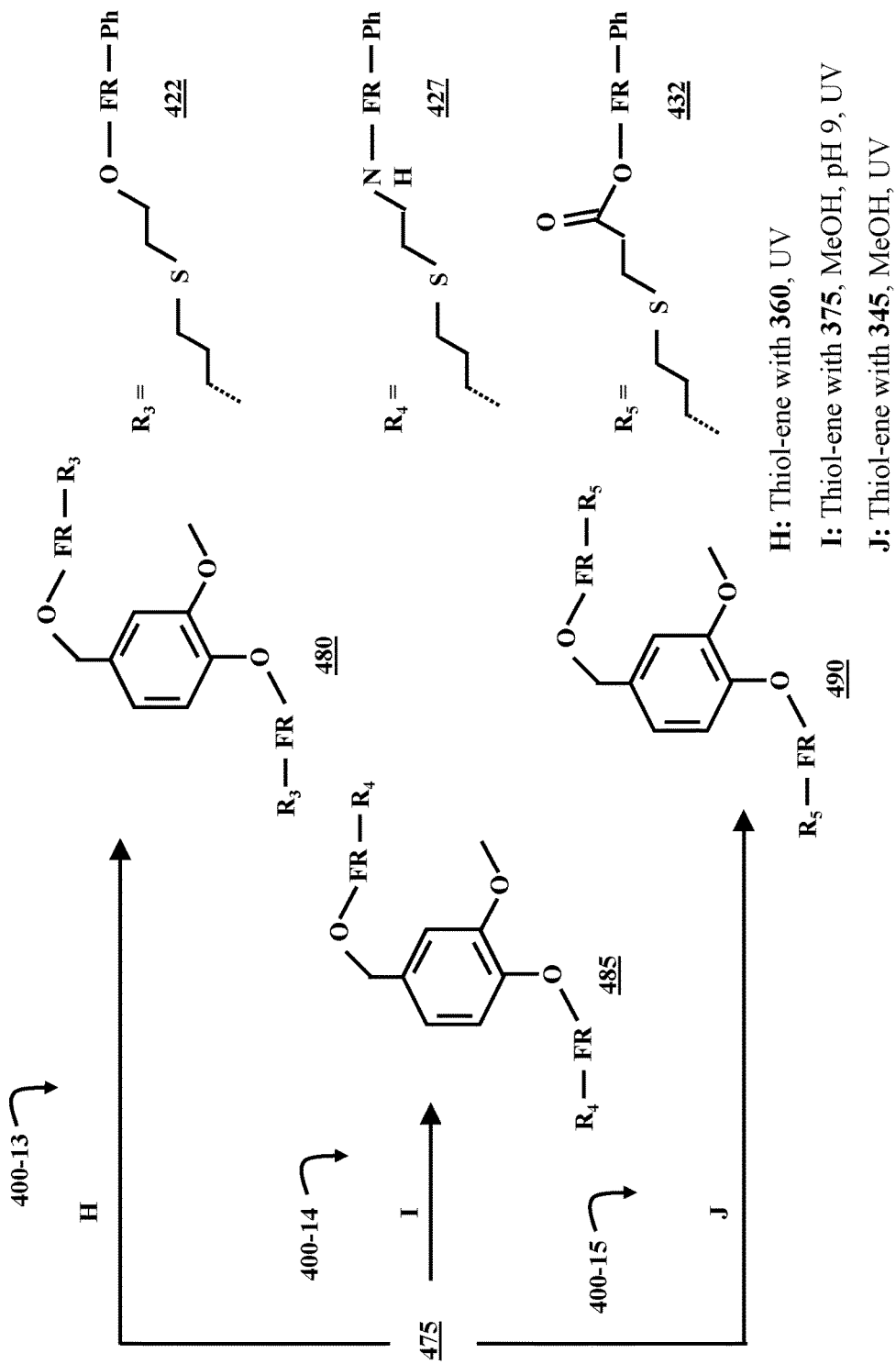
FIG. 4F is a chemical reaction diagram illustrating three processes of synthesizing thioether-linked flame-retardant benzyl alcohol vanillin-derived small molecules, according to some embodiments of the present disclosure.

FIG. 4F is a chemical reaction diagram illustrating three processes 400-13, 400-14, and 400-15 of synthesizing thioether-linked flame-retardant benzyl alcohol vanillin-derived small molecule, according to embodiments of the present disclosure. Each process is a thiol-ene reaction between the allyl-substituted flame-retardant benzyl alcohol vanillin-derived small molecule 475 and a flame-retardant thiol molecule. The syntheses and structures of the flame-retardant thiol molecules are discussed in greater detail with regard to FIGS. 3C and 3D.

In process 400-13, the allyl-substituted flame-retardant benzyl alcohol vanillin-derived small molecule 475 is reacted with the hydroxy-derived flame-retardant thiol molecule 360 under UV light. The resulting thioether-linked flame-retardant benzyl alcohol vanillin-derived small molecule 480 has an $R_3$ group 422 that corresponds to the hydroxy-derived flame-retardant thiol molecule 360. In process 400-14, the allyl-substituted flame-retardant benzyl alcohol vanillin-derived small molecule 475 is reacted with the amino-derived flame-retardant thiol molecule 375 in a pH 9 methanol (MeOH) solution under UV light. The resulting thioether-linked flame-retardant benzyl alcohol vanillin-derived small molecule 485 has an $R_4$ group 427 that corresponds to the amino-derived flame-retardant thiol molecule 375. In process 400-15, the allyl-substituted flame-retardant benzyl alcohol vanillin-derived small molecule 475 is reacted with the carboxylic acid-derived flame-retardant thiol molecule 345 under UV light in a methanol (MeOH) solution. The resulting thioether-linked flame-retardant benzyl alcohol vanillin-derived small molecule 490 has an $R_5$ group 432 that corresponds to the carboxylic acid-derived flame-retardant thiol molecule 345.

In some embodiments, the processes of forming substituted flame-retardant vanillin-derived small molecules illustrated in FIGS. 4A, 4C, and 4E are carried out with a mixture of either both DPCPa and DPCPo or both phosphate-240-1 and phosphonate-based 240-2 flame-retardant molecules. Carrying out processes 400-1, 400-6, and 400-11 with a mixture of DPCPa and DPCPo can result in the production of phenyl-substituted flame-retardant vanillin-derived small molecules with both phosphoryl and phosphonyl FR groups. Likewise, combining the phosphate-240-1 and phosphonate-based 240-2 flame retardant molecules in processes 400-2, 400-7, and 400-12 can result in allyl-substituted flame-retardant vanillin vanillin-derived small molecules with both phosphoryl and phosphonyl FR groups.

However, in some instances, adding a mixture of phosphate-240-1 and phosphonate-based 240-2 flame retardant molecules (or DPCPa and DPCPo) can result in the production of flame-retardant vanillin-derived small molecules 102 with all phosphoryl or all phosphonyl FR groups. Additionally, adding both phosphate- and phosphonate-based flame retardant molecules to the reaction can yield a mixture of products that includes some combination of flame-retardant vanillin-derived small molecules with either all phosphoryl or all phosphonyl FR groups and flame-retardant vanillin-derived small molecules 102 with both phosphoryl and phosphonyl FR groups.

Further, in some embodiments, the processes of forming thioether-linked flame-retardant vanillin-derived small molecules illustrated in FIGS. 4B, 4D, and 4F are carried out with mixtures of more than one type of thiol molecule. This can result in the production of thioether-linked flame-retardant vanillin-derived small molecules that have two different types of thioether-linked FR group. However, in some instances, adding more than one type of thiol molecule to the reaction mixture can result in thioether-linked flame-retardant vanillin-derived small molecules that have two identical thioether-linked FR groups. Adding more than one type of thiol molecule to the reaction mixture can also result in a mixture of products that includes some combination of vanillin-derived small molecules with either two different thioether-linked FR groups or two identical thioether-linked FR groups.

The flame-retardant vanillin-derived small molecules 102 disclosed herein can be combined with polymers and resins that have a variety of applications. These polymers and resins are made flame-retardant by the addition of the flame-retardant vanillin-derived small molecules 102. The flame-retardant polymers and resins can be used in a number of devices. The flame-retardant vanillin-derived small molecules 102 can be added to the polymers and resins during blending, curing, foaming, extrusion, or other processing techniques.

One example of a polymer that can be made flame-retardant by the addition of flame-retardant vanillin-derived small molecules 102 is polycarbonate-acrylonitrile butadiene styrene (PC-ABS), a plastic that is often used in electronics hardware. Flame-retardant vanillin-derived small molecules 102 can also be incorporated into polyurethane. Polyurethane is a versatile polymer used in applications that include acoustic dampening, cushioning, plastics, synthetic fibers, insulation, adhesives, etc. The vanillin-based flame-resistant small molecules 102 can also be added to adhesives such as bio-adhesives, elastomers, thermoplastics, emulsions, thermosets, etc. Further, materials containing the vanillin-based flame-resistant small molecules 102 can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating vanillin-based flame-retardant small molecules 102. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polyurethane, a polycarbonate, a polyester, a polyacrylate, a polyimide, a polyamide, a polyurea, a poly(vinyl-ester), etc. Flame-retardant vanillin-derived small molecules 102 can be added to the resin in order to prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame-retardant vanillin-derived small molecule with a formula of:

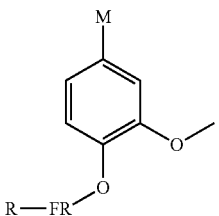

wherein M is a flame-retardant substituent;

wherein FR is a phosphorus-based moiety; and wherein R is a substituent selected from a group consisting of a phenyl substituent, an allyl substituent, and a thioether substituent.

2. The flame-retardant vanillin-derived small molecule of claim 1, wherein the M is a substituent selected from a group consisting of substituents with formulas of:

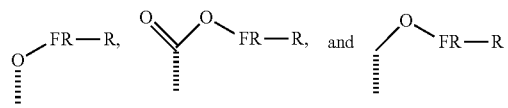

wherein FR is a second phosphorus-based moiety; and wherein R is a second substituent selected from the group consisting of the phenyl substituent, the allyl substituent, and the thioether substituent.

3. The flame-retardant vanillin-derived small molecule of claim 1, wherein the PR is a phosphoryl moiety with a formula of:

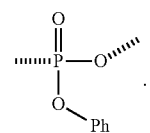

4. The flame-retardant vanillin-derived small molecule of claim 1, wherein the FR is a phosphonyl moiety with a formula of:

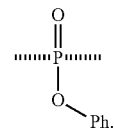

5. The flame-retardant vanillin-derived small molecule of claim 1, wherein the thioether substituent is selected from a group consisting of thioether substituents with formulas of:

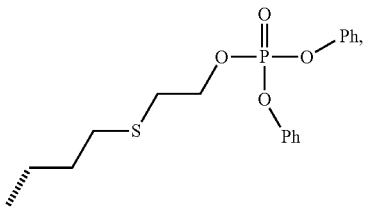

-continued
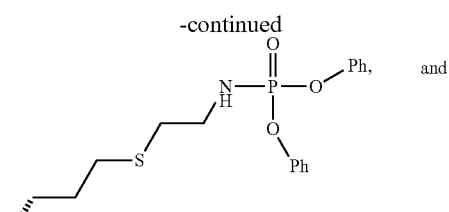
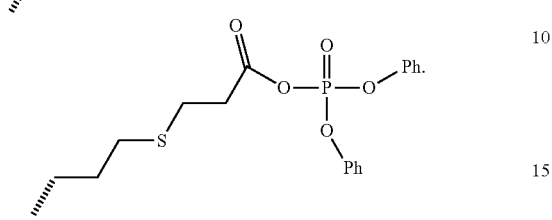
6. The flame-retardant vanillin-derived small molecule of claim 1, wherein, the vanillin from a bio-based source is a starting material for the flame-retardant vanillin-derived small molecule.
7. The flame-retardant vanillin-derived small molecule of claim 1, wherein the flame-retardant vanillin-derived small molecule is blended with a polymer.
* * * * *